US010721966B2

(12) United States Patent
Li et al.

(10) Patent No.: US 10,721,966 B2
(45) Date of Patent: Jul. 28, 2020

(54) ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Changzheng Dai, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 700 days.

(21) Appl. No.: 15/469,483

(22) Filed: Mar. 24, 2017

(65) Prior Publication Data
US 2017/0196272 A1    Jul. 13, 2017

(30) Foreign Application Priority Data
Mar. 31, 2016  (CN) ...................... 2016 2 0263112 U

(51) Int. Cl.
A24F 47/00    (2020.01)
(52) U.S. Cl.
CPC .......... *A24F 47/008* (2013.01); *A24F 47/002* (2013.01); *A61M 2209/045* (2013.01)
(58) Field of Classification Search
CPC ........ A24F 47/008; A24F 47/00; A24F 47/02; A24F 9/16; A24F 13/02; A24F 13/14

USPC ................ 392/386, 394–399, 401–404, 409; 131/217, 273, 329
See application file for complete search history.

(56) References Cited

U.S. PATENT DOCUMENTS

2014/0360514 A1\* 12/2014 Zhu ...................... A24F 47/008
131/329

FOREIGN PATENT DOCUMENTS

WO    WO-2015157938 A1 \* 10/2015 ........... A24F 47/004

\* cited by examiner

*Primary Examiner* — Tu B Hoang
*Assistant Examiner* — Diallo I Duniver
(74) *Attorney, Agent, or Firm* — Cheng-Ju Chiang

(57) ABSTRACT

An exemplary atomizer includes a housing, a sealing cover, an atomizing element, an air passage, and an liquid injecting opening. The housing has a first end and an opposite second end. The second end is configured for connecting with a power supply. The housing defines a liquid chamber configured for containing tobacco liquid. The sealing cover is threadedly coupled with the first end. The atomizing element is configured for atomizing the tobacco liquid to form aerosol. The liquid injecting opening is defined in the first end. The sealing cover is configured for sealing the liquid injecting opening. The sealing cover includes a device configured for preventing children from screwing off the sealing cover. The sealing cover can be screwed off via an outer surface thereof only when an external force is exerted on the device to change an internal structural relationship of the device.

12 Claims, 9 Drawing Sheets

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

Refillable atomizers are more popular and environmentally-friendly than disposable atomizers. A typical refillable atomizer includes a liquid injecting opening, and a sealing cover is used to seal the liquid injecting opening, avoiding leakage of tobacco liquid inside. However, when children get the refillable atomizer, the children may screw off the sealing cover easily, and drink the tobacco liquid mistaken for food. Accordingly, such refillable atomizer may be harmful for kids.

What are needed, therefore, are an atomizer and an electronic cigarette using same, which can overcome the above shortcomings.

SUMMARY

An exemplary atomizer includes a housing, a sealing cover, an atomizing element, an air passage, and an liquid injecting opening. The housing has a first end and an opposite second end. The second end is configured for connecting with a power supply. The housing defines a liquid chamber configured for containing tobacco liquid. The sealing cover is threadedly coupled with the first end. The atomizing element is configured for atomizing the tobacco liquid to form aerosol. The liquid injecting opening is defined in the first end. The sealing cover is configured for sealing the liquid injecting opening. The sealing cover includes a device configured for preventing children from screwing off the sealing cover. The sealing cover can be screwed off via an outer surface thereof only when an external force is exerted on the device to change an internal structural relationship of the device.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
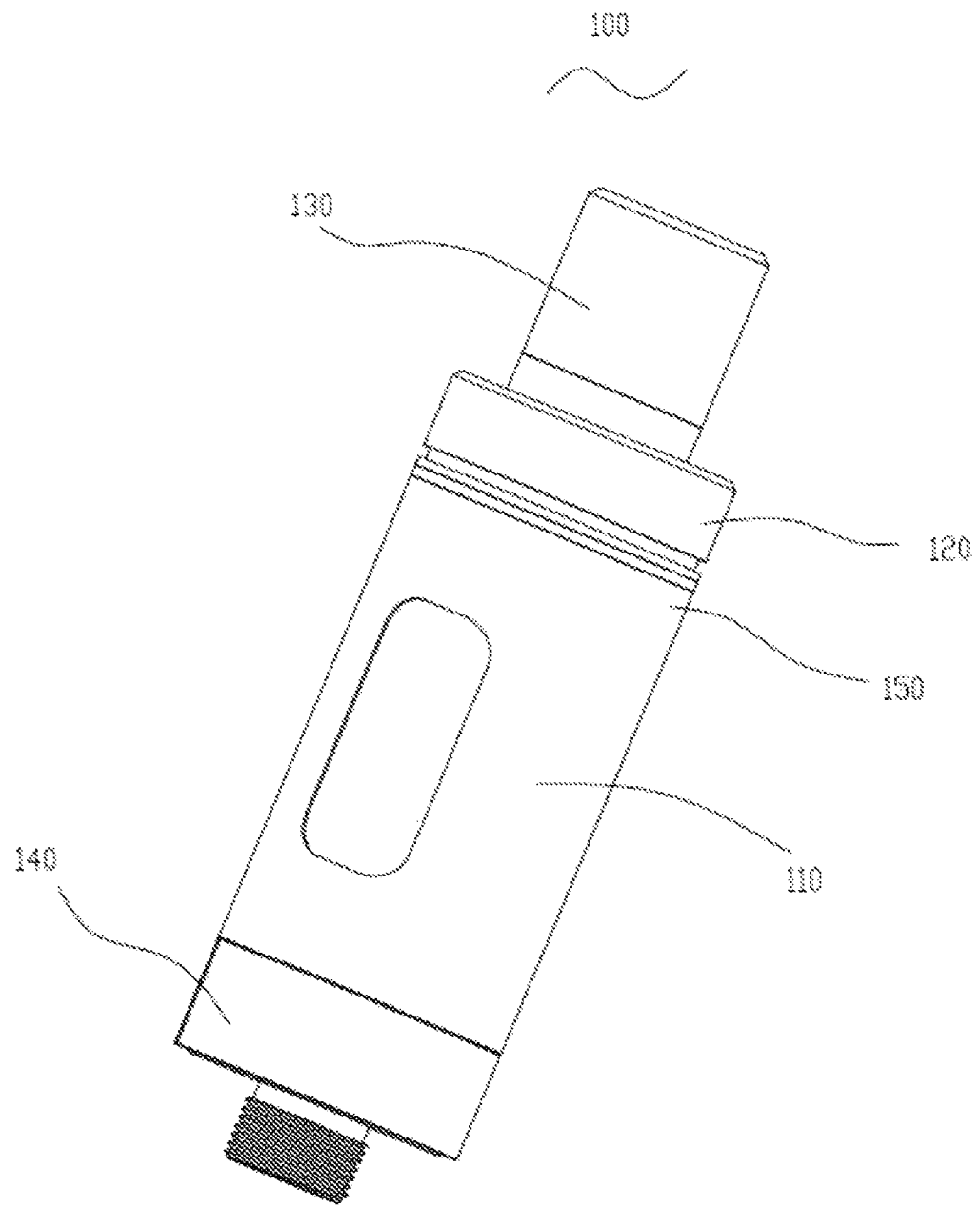
FIG. 1 is a perspective view of an atomizer according to a first embodiment, including a sealing cover.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
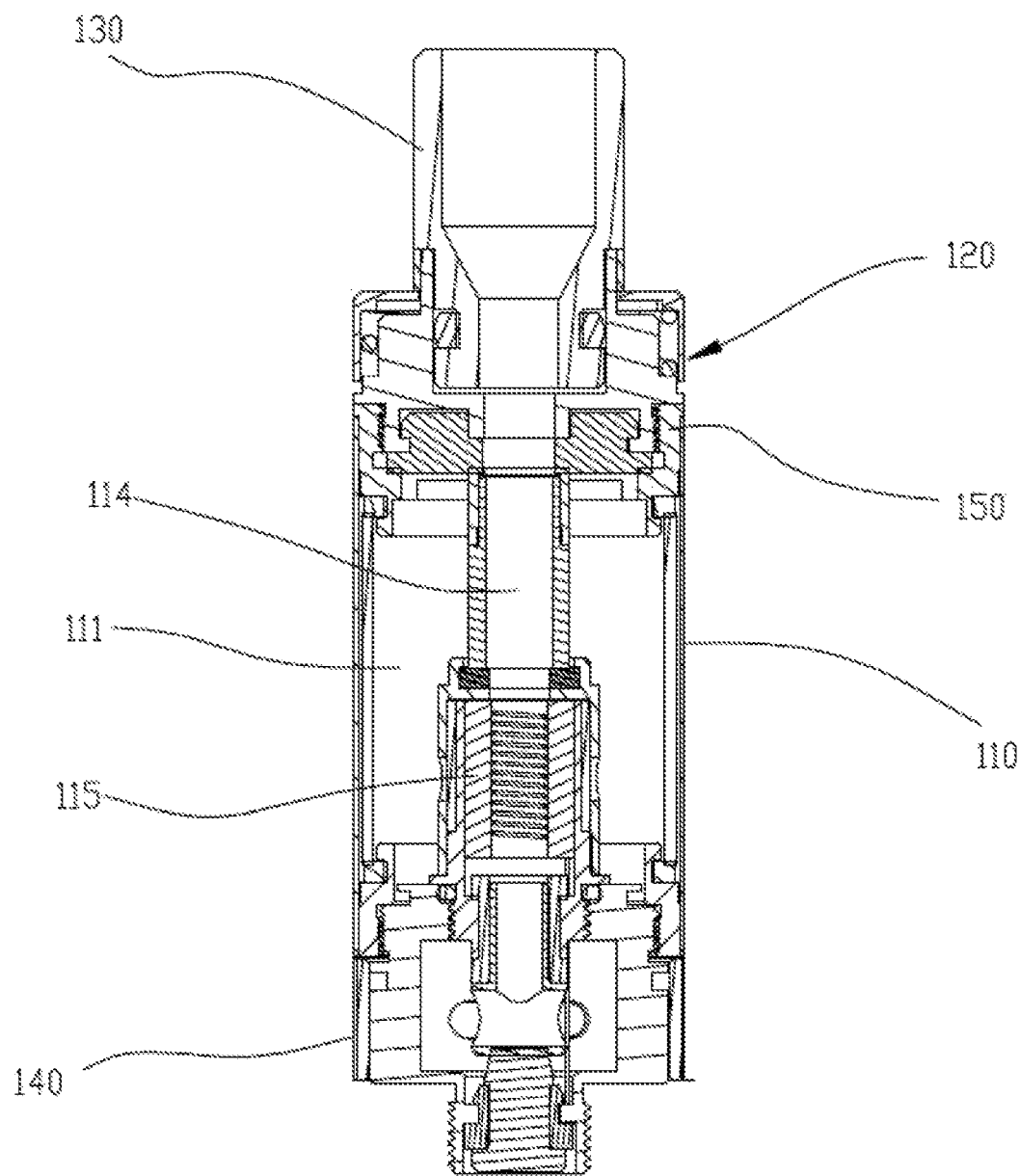
FIG. 2 is a cross-sectional view of the atomizer of FIG. 1.
Figure 3:
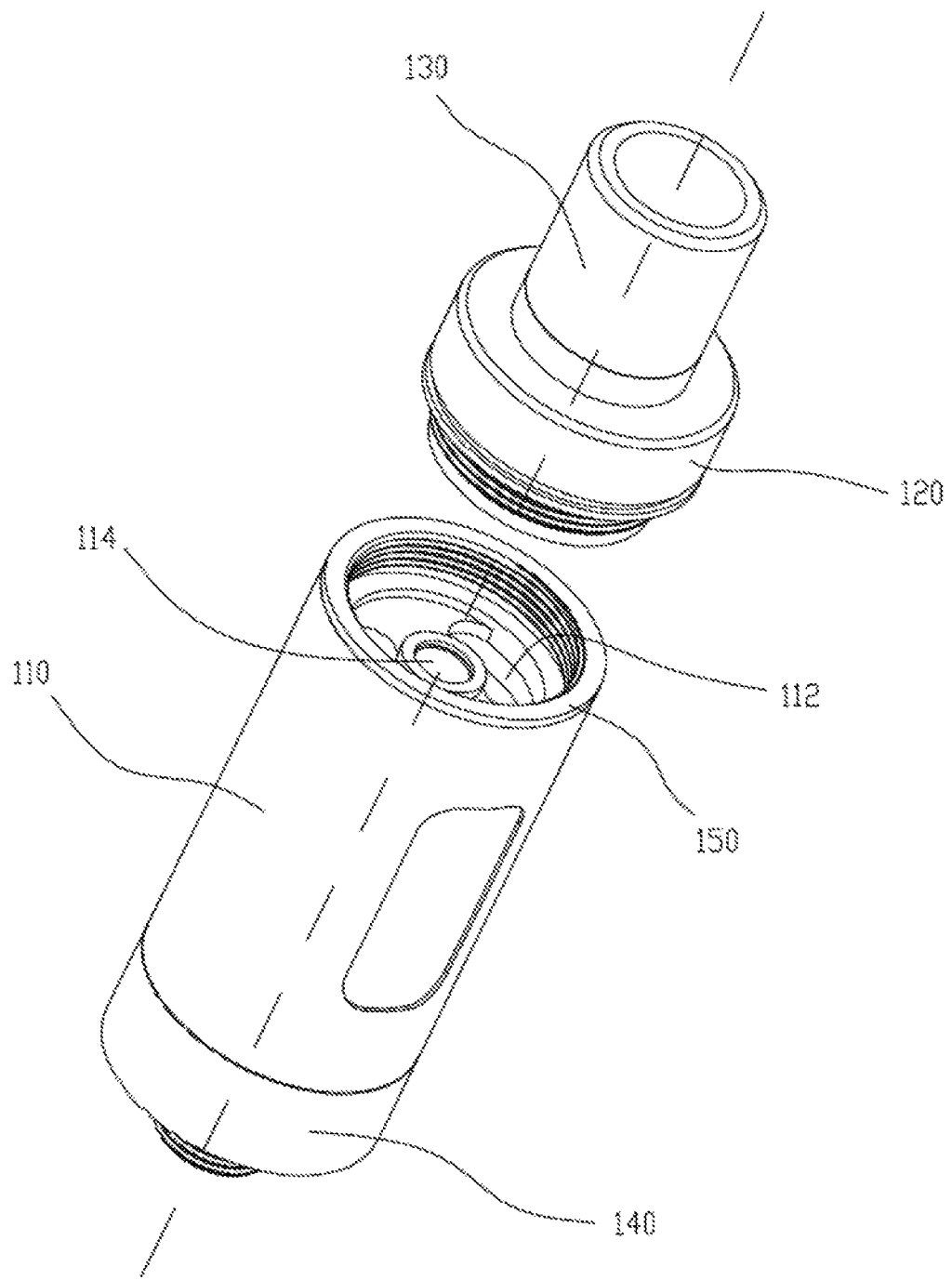
FIG. 3 is a perspective view of the atomizer of FIG. 1 when the sealing cover is detached.

Referring to FIGS. 1-3, an atomizer 100 is shown. The atomizer 100 includes a housing 110, a sealing cover 120. The housing 110 includes a first end 150 and a second end 140. The sealing cover 120 is threadedly coupled to the first end 150. The second end 140 is configured (i.e., structured and arranged) for connecting with a power supply 200. The housing 110 defines a liquid chamber 111 for containing tobacco liquid, and an air passage 114. An atomizing element 115 is provided in the housing 110. The atomizing element 115 is configured for atomizing the tobacco liquid to form aerosol. The first end 150 defines a liquid injecting opening 112 in communication with the liquid chamber 111. When the sealing cover 120 is connected to the first end 150, the sealing cover 120 seals the liquid injecting opening 112, thus avoiding liquid leakage. The sealing cover 120 further includes a device configured for preventing children from screwing off the sealing cover 120. The sealing cover 120 can be screwed off via an outer surface thereof only when an external force is exerted on the device to change an internal structural relationship of the device. The sealing cover 120 further includes a mouthpiece 130, and the aerosol can be expelled via the mouthpiece 130.

Figure 4:
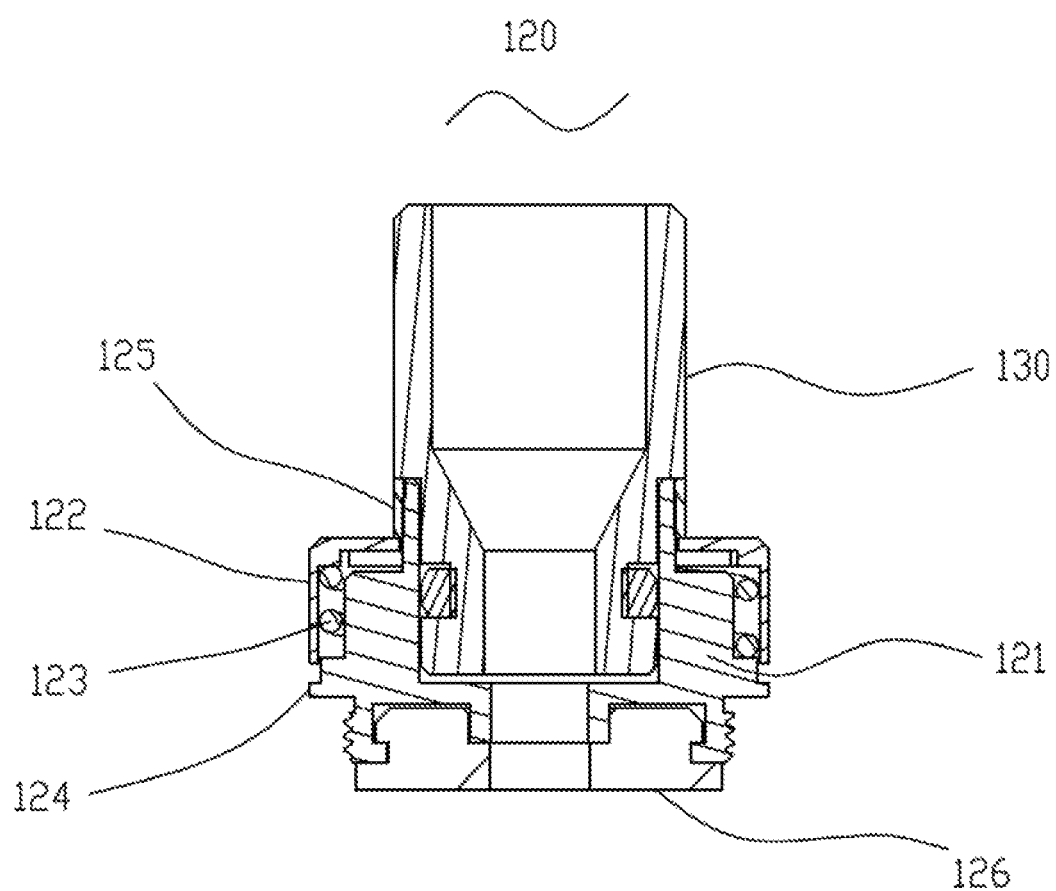
FIG. 4 is a cross-sectional view of the sealing cover, including a main body and a protective cover.
Figure 5:
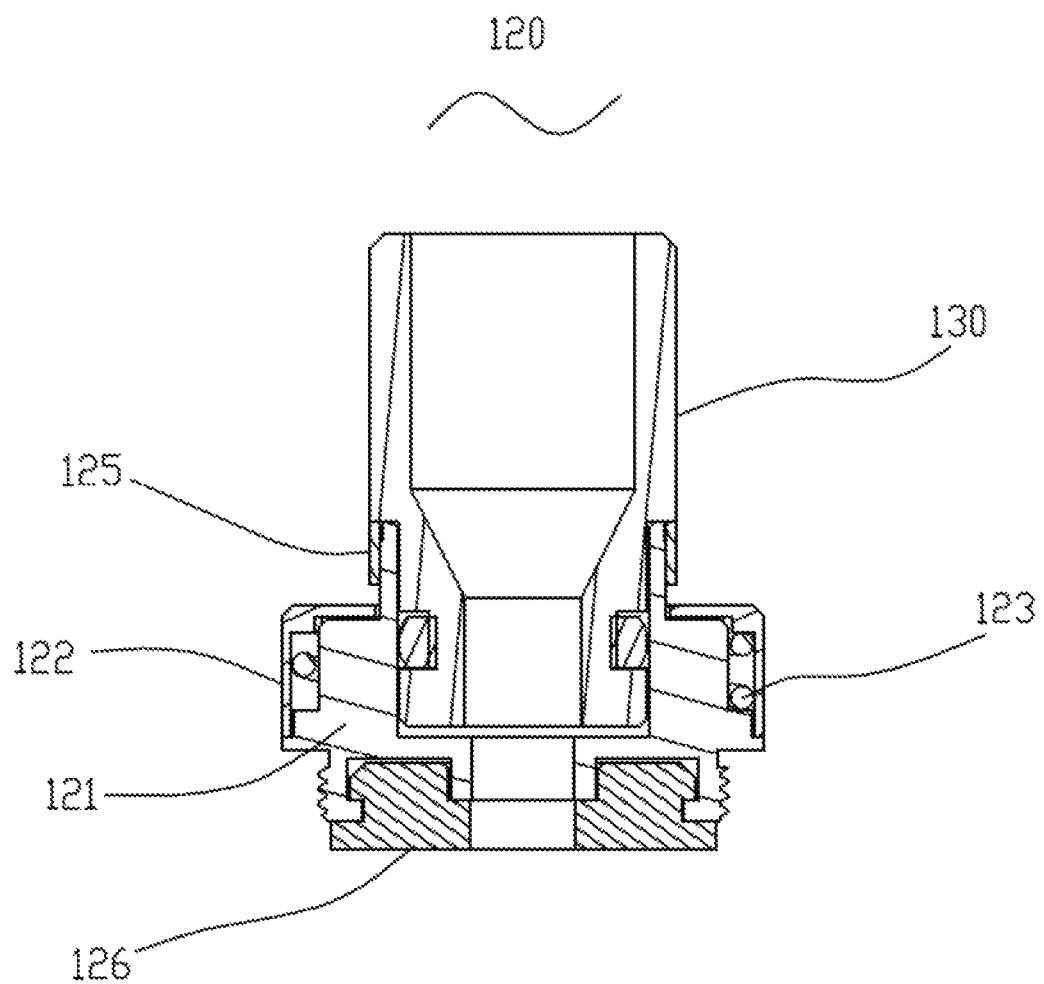
FIG. 5 is a cross-sectional view of the sealing cover when the protective cover is coupled with the main body.
Figure 6:
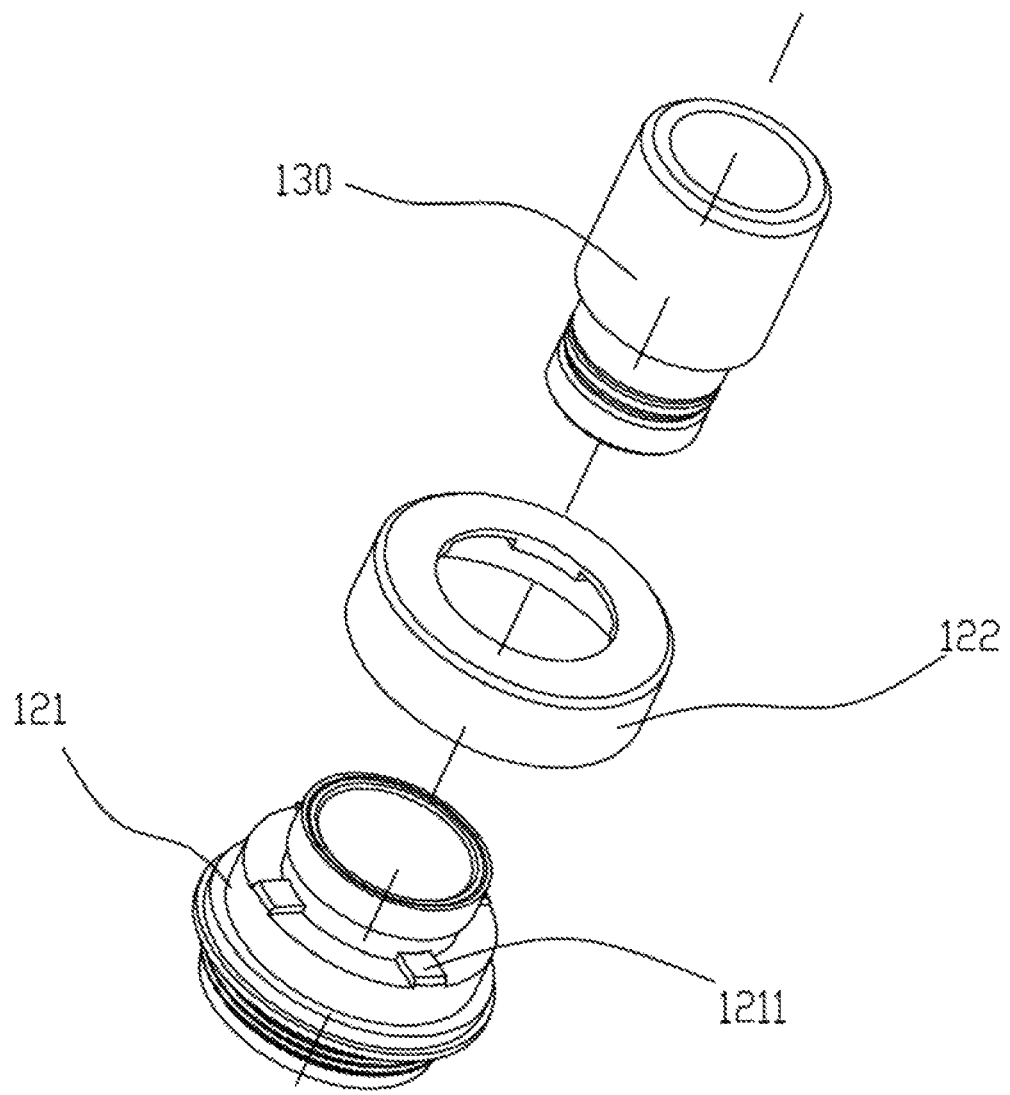
FIG. 6 is an exploded perspective view of the sealing cover.
Figure 7:
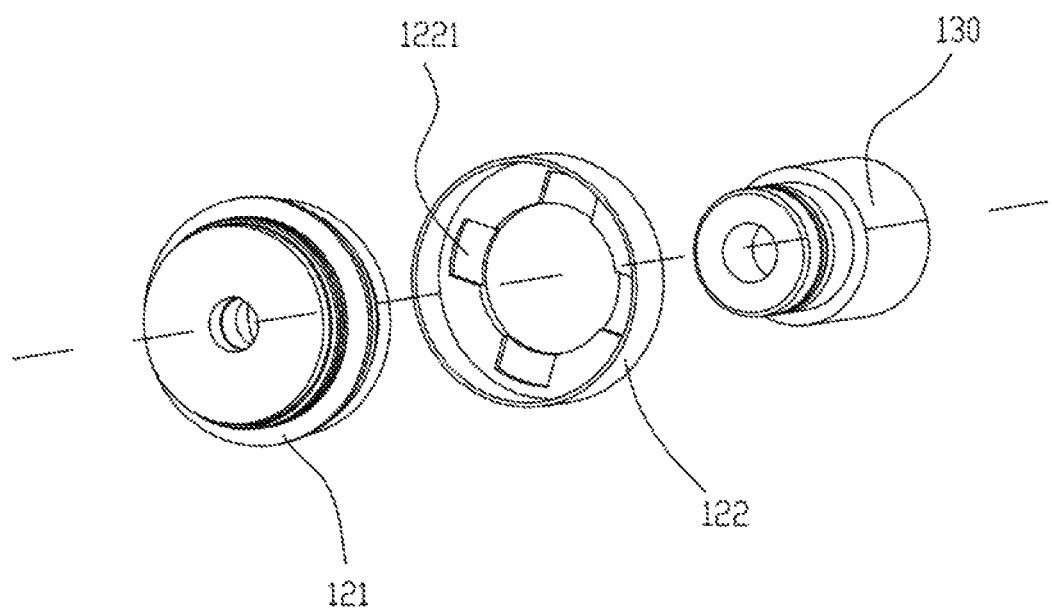
FIG. 7 is an exploded perspective view of the sealing cover view from another angle.

Referring to FIGS. 4-7, the sealing cover 120 includes a main body 121, and a protective cover 122. The device includes a spring 123, a first protrusion 1211, and a groove 1221. The spring 123 is arranged between the main body 121 and the protective cover 122. The first protrusion 1211 is arranged on one of the main body 121 and the protective cover 122. The groove 1221 is defined in the other of the main body 121 and the protective cover 122. In the present embodiment, the first protrusions 1211 are arranged on the main body 121, and the grooves 1221 are defined in the protective cover 122. Referring to FIG. 4, the spring 123 supports the protective cover 122, so that the groove 1221 is disengaged with the first protrusions 1211. In this position, the main body 121 cannot be screwed off via the protective cover 122. Referring to FIG. 5, when the protective cover 122 is pressed towards the main body 121 along an axial direction of the main body 121 to overcome an elastic force of the spring 123, the first protrusions 1211 are engaged in the grooves 1221, and the main body 121 can be driven to rotate by the protective cover 122. In this way, the sealing cover 120 is detached from the first end 150. The mouthpiece 130 is detachably connected to an end of the main body 121.

The main body 121 further includes a first limiting component 125 and a second limiting component 124. The first limiting component 125 abuts against the protective cover 122 and is configured for limiting an axial position of the protective cover 122 when the protective cover 122 is pushed by the spring 123. The second limiting component 124 is configured for limiting an axial position of the protective cover 122 when an external force is exerted on the protective cover 122.

In the present embodiment, the second limiting component 124 is a second protrusion integrally formed with the main body 121. An outer surface of the second protrusion matches with an external diameter of the protective cover 122. The first limiting component 125 is an annular body fixedly nesting the main body 121, and abuts against an outer surface of the protective cover 122.

Referring to FIG. 4, the main body 121 further includes a flexible sealing element 126 configured for sealing the liquid injecting opening 112, thus avoiding liquid leakage. The sealing element 126 may be made of silicone.

Because the atomizer 100 includes the device, the sealing cover 120 can be screwed off via an outer surface of the sealing cover 120. Accordingly, it is prevented that children screw off the sealing cover 120, and drink the tobacco liquid mistaken for food. Also, liquid leakage is prevented for misoperation of the children.

Figure 8:
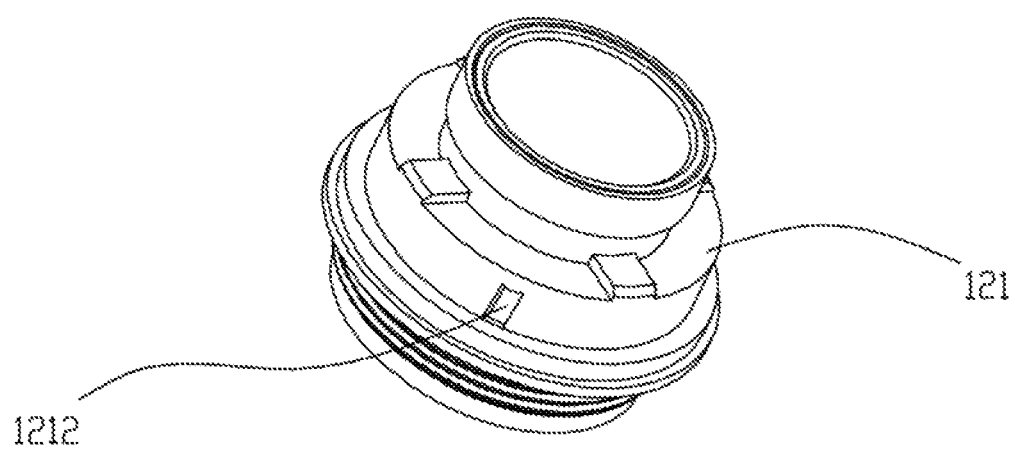
FIG. 8 is a perspective view of a main body according to a second embodiment.
Figure 9:
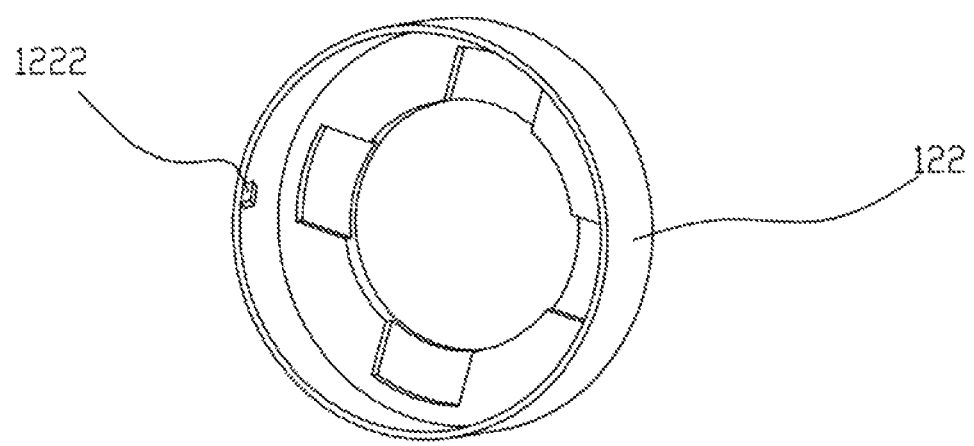
FIG. 9 is a perspective view of a protective cover according to the second embodiment.

It is to be understood that, in other embodiments, the external force may also be a pulling force exerted on the protective cover 122. For example, referring to FIGS. 8-9, the second limiting component 124 includes a positioning block 1222 fixed on one of the main body 121 and the protective cover 122, and a sliding slot 1212 defined in the other of the main body 121 and the protective cover 122. The sliding slot 1212 matches with the positioning block 1222. The sliding slot 1212 is configured for restricting a moving position of the positioning block 1222, thus limiting a moving position of the protective cover 122.

Figure 10:
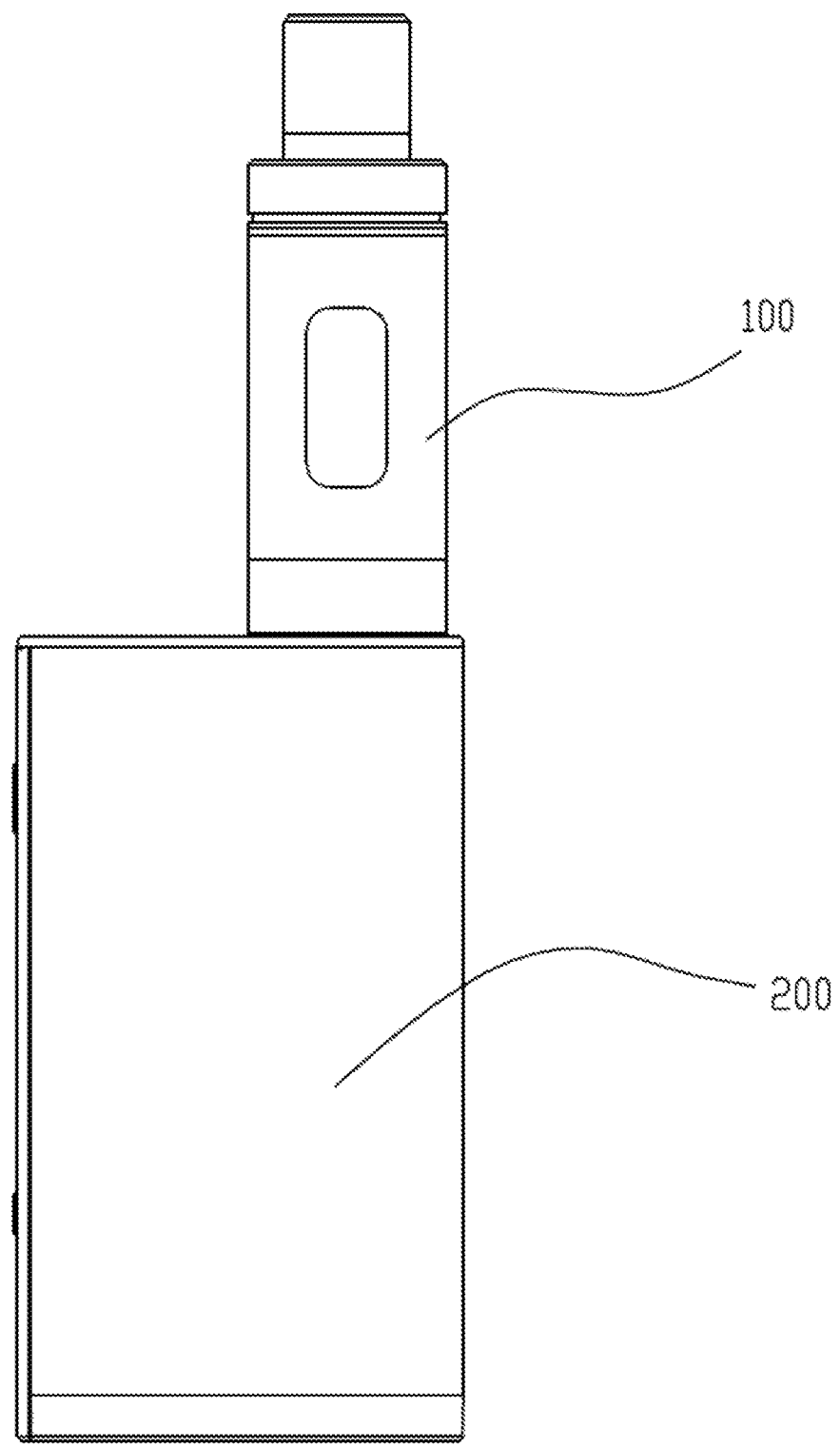
FIG. 10 is a front view of an electronic cigarette according to a third embodiment.

Referring to FIG. 10, an electronic cigarette according to a third embodiment is shown. The electronic cigarette includes an atomizer 100 of the first embodiment, and a power supply 200. The power supply 200 is detachably coupled with the atomizer 100, e.g., via screw threads. The power supply 200 is configured for supplying the atomizer 100 power.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer for an electronic cigarette, comprising:
a housing having a first end and an opposite second end, the second end being configured for connecting with a power supply, the housing defining a liquid chamber configured for containing tobacco liquid;
a sealing cover threadedly coupled with the first end along a preset rotation direction;
an atomizing element arranged in the housing, the atomizing element being configured for atomizing the tobacco liquid to form aerosol;
an air passage defined in the housing; and
a liquid injecting opening defined in the first end, the liquid injecting opening being in communication with the liquid chamber, the sealing cover being configured for sealing the liquid injecting opening;
wherein the sealing cover comprises a first protrusion and a groove configured for preventing children from screwing off the sealing cover, the sealing cover can be screwed off only when an external force is exerted on the sealing cover to make the first protrusion moving to engage with the groove along an axial direction perpendicular to the rotation direction of the sealing cover the sealing cover subsequently rotates along the rotation direction thereof and is screwed off from the first end of the housing during engagement of the first protrusion with the groove.

2. The atomizer according to claim 1, wherein the sealing cover further comprises a main body threadedly coupled to the first end, and a protective cover nesting the main body; the sealing cover further comprises a spring, the spring is arranged between the main body and the protective cover, one of the main body and the protective cover is made to equip with the first protrusion, and the other of the main body and the protective cover is made to equip with the groove, the groove matches with the first protrusion; the spring makes the groove disengaged with the first protrusion; when an external force is exerted on the main body along an axial direction of the main body to overcome an elastic force of the spring, the first protrusion is engaged with the groove, so that the protective cover is capable of driving the main body to rotate, thus separating the sealing cover from the first end.

3. The atomizer according to claim 2, wherein the main body further comprises a first limiting component, the first limiting component abuts against the protective cover, and is configured for limiting an axial position of the protective cover when the protective cover is pushed by the spring.

4. The atomizer according to claim 2, wherein the main body further comprises a second limiting component, and the second limiting component is configured for limiting an axial position of the protective cover when the external force is exerted on the protective cover.

5. The atomizer according to claim 4, wherein the second limiting component is a second protrusion integrally formed with the main body, and an outer surface of the second protrusion matches with an external diameter of the protective cover.

6. The atomizer according to claim 4, wherein the second limiting component comprises a positioning block arranged on one of the main body and the protective cover, and a sliding slot defined in the other of the main body and the protective cover; the sliding slot matches with the positioning block, and the sliding slot is configured for restricting a moving position of the positioning block.

7. The atomizer according to claim 2, further comprising a flexible sealing element, wherein the sealing element is configured for sealing the liquid injecting opening.

8. An electronic cigarette, comprising:
an atomizer according to claim 1; and
a power supply configured for feeding the atomizer power.

9. The electronic cigarette according to claim 8, wherein the sealing cover further comprises a main body threadedly coupled to the first end, and a protective cover nesting the main body; the sealing cover further comprises a spring, the spring is arranged between the main body and the protective cover, one of the main body and the protective cover is made to equip with the first protrusion, and the other of the main body and the protective cover is made to equip with the groove, the groove matches with the first protrusion; the spring makes the groove disengaged with the first protrusion; when an external force is exerted on the main body along an axial direction of the main body to overcome an elastic force of the spring, the first protrusion is engaged with the groove, so that the protective cover is capable of driving the main body to rotate, thus separating the sealing cover from the first end.

10. The electronic cigarette according to claim 9, wherein the main body further comprises a first limiting component, the first limiting component abuts against the protective cover, and is configured for limiting an axial position of the protective cover when the protective cover is pushed by the spring.

11. The electronic cigarette according to claim 9, wherein the main body further comprises a second limiting component, and the second limiting component is configured for limiting an axial position of the protective cover when the external force is exerted on the protective cover.

12. The electronic cigarette according to claim 11, wherein the second limiting component is a second protrusion integrally formed with the main body, and an outer surface of the second protrusion matches with an external diameter of the protective cover.

* * * * *